US010082507B2

(12) United States Patent
Sia et al.

(10) Patent No.: US 10,082,507 B2
(45) **Date of Patent: *Sep. 25, 2018**

(54) ASSAY DEVICE AND METHOD

(71) Applicant: President and Fellows of Harvard College, Cambridge, MA (US)

(72) Inventors: Samuel K. Sia, New York, NY (US); Vincent Linder, Tewksbury, MA (US); Babak Parviz, Mountain View, CA (US); Adam Siegel, New York, NY (US); George M. Whitesides, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 418 days.

This patent is subject to a terminal disclaimer.

(21) Appl. No.: 14/042,606

(22) Filed: Sep. 30, 2013

(65) Prior Publication Data

US 2014/0134603 A1 May 15, 2014

Related U.S. Application Data

(60) Continuation of application No. 12/769,489, filed on Apr. 28, 2010, now Pat. No. 8,574,924, which is a (Continued)

(51) Int. Cl.
*G01N 33/569* (2006.01)
*B01L 3/00* (2006.01)
(Continued)

(52) U.S. Cl.
CPC .. *G01N 33/56988* (2013.01); *B01L 3/502707* (2013.01); *G01N 21/05* (2013.01); (Continued)

(58) Field of Classification Search
CPC ........... G01N 33/56988; G01N 33/543; G01N 33/585; G01N 33/5302; G01N 21/59; (Continued)

(56) References Cited

U.S. PATENT DOCUMENTS 4,517,302 A 5/1985 Saros
4,687,736 A 8/1987 Newman et al.
(Continued)

FOREIGN PATENT DOCUMENTS

EP 461174 B1 12/1991
EP 481020 B1 4/1992
(Continued)

OTHER PUBLICATIONS

International Search Report and Written Opinion for PCT/US2004/043585 dated May 6, 2005.
(Continued)

*Primary Examiner* — Melanie Yu Brown
(74) *Attorney, Agent, or Firm* — Wolf, Greenfield & Sacks, P.C.

(57) ABSTRACT

An assay method is described, which comprises the steps of immobilizing a binding partner (e.g., an antigen or antibody) for an analyte to be detected (e.g., an antibody or antigen) on a portion of a surface of a microfluidic chamber; passing a fluid sample over the surface and allowing the analyte to bind to the binding partner; allowing a metal colloid, e.g., a gold-conjugated antibody, to associate with the bound analyte; flowing a metal solution, e.g., a silver solution, over the surface such as to form an opaque metallic layer; and detecting the presence of said metallic layer, e.g., by visual inspection or by measuring light transmission through the layer, conductivity or resistance of the layer, or metal concentration in the metal solution after flowing the metal solution over the surface.

44 Claims, 6 Drawing Sheets

5 mm
laser diode
sample on a microchip (aligned on pinhole)
glass
optical IC
transmitter electronics
receiver electronics
liquid crystal display
9 V battery
reduced silver
gold-labeled antibody (gold-anti-rabbit IgG)
analyte (rabbit IgG)
polystyrene surface

Related U.S. Application Data division of application No. 10/584,819, filed as application No. PCT/US2004/043585 on Dec. 29, 2004, now Pat. No. 7,736,890.

(60) Provisional application No. 60/539,416, filed on Jan. 26, 2004, provisional application No. 60/533,627, filed on Dec. 31, 2003.

(51) Int. Cl.

| | |
|---|---|
| ***G01N 21/05*** | (2006.01) |
| ***G01N 21/59*** | (2006.01) |
| ***G01N 33/53*** | (2006.01) |
| ***G01N 33/58*** | (2006.01) |
| ***G01N 33/543*** | (2006.01) |
| *G01N 21/03* | (2006.01) |

(52) U.S. Cl.

CPC ......... *G01N 21/59* (2013.01); *G01N 33/5302* (2013.01); *G01N 33/543* (2013.01); *G01N 33/585* (2013.01); *B01L 2300/0822* (2013.01); *B01L 2300/168* (2013.01); *G01N 2021/0346* (2013.01); *Y10T 436/11* (2015.01); *Y10T 436/117497* (2015.01); *Y10T 436/118339* (2015.01)

(58) Field of Classification Search

CPC .............. G01N 21/05; B01L 3/502707; Y10T 436/117497; Y10T 436/11; Y10T 436/118339

See application file for complete search history.

(56) References Cited

U.S. PATENT DOCUMENTS

| | | | | |
|---|---|---|---|---|
| 4,775,636 | A | 10/1988 | Moeremans et al. | |
| 4,908,242 | A | 3/1990 | Hughes et al. | |
| 4,931,384 | A | 6/1990 | Layton et al. | |
| 4,963,498 | A | 10/1990 | Hillman et al. | |
| 5,116,734 | A | 5/1992 | Higgs et al. | |
| 5,147,607 | A | 9/1992 | Mochida | |
| 5,318,621 | A | 6/1994 | Krulik et al. | |
| 5,399,497 | A | 3/1995 | Kumar et al. | |
| 5,441,896 | A | 8/1995 | Noppe et al. | |
| 5,491,098 | A | 2/1996 | Noppe et al. | |
| 5,571,410 | A | 11/1996 | Swedberg et al. | |
| 5,595,878 | A | 1/1997 | Sood et al. | |
| 5,607,863 | A | 3/1997 | Chandler | |
| 5,637,469 | A | 6/1997 | Wilding et al. | |
| 5,637,508 | A | 6/1997 | Kidwell et al. | |
| 5,866,345 | A | 2/1999 | Wilding et al. | |
| 5,939,252 | A | 8/1999 | Lennon et al. | |
| 5,957,579 | A | 9/1999 | Kopf-Sill et al. | |
| 6,025,202 | A | 2/2000 | Natan | |
| 6,103,199 | A | 8/2000 | Bjornson et al. | |
| 6,146,489 | A | 11/2000 | Wirth | |
| 6,146,589 | A | 11/2000 | Chandler | |
| 6,186,660 | B1 | 2/2001 | Kopf-Sill et al. | |
| 6,214,560 | B1 | 4/2001 | Yguerabide et al. | |
| 6,241,560 | B1 | 6/2001 | Furusawa et al. | |
| 6,277,489 | B1 | 8/2001 | Abbott et al. | |
| 6,333,200 | B1 | 12/2001 | Kaler et al. | |
| 6,361,958 | B1 | 3/2002 | Shieh et al. | |
| 6,468,657 | B1 | 10/2002 | Hou et al. | |
| 6,479,299 | B1 | 11/2002 | Parce et al. | |
| 6,488,872 | B1 | 12/2002 | Beebe et al. | |
| 6,488,894 | B1 | 12/2002 | Miethe et al. | |
| 6,488,896 | B2 | 12/2002 | Weigl et al. | |
| 6,551,841 | B1 | 4/2003 | Wilding et al. | |
| 6,602,669 | B2 | 8/2003 | Letsinger et al. | |
| 6,613,512 | B1 | 9/2003 | Kopf-Sill et al. | |
| 6,685,943 | B1 * | 2/2004 | Hook | A61K 39/085 424/184.1 |
| 6,709,869 | B2 | 3/2004 | Mian et al. | |
| 6,716,620 | B2 | 4/2004 | Bashir et al. | |
| 6,742,661 | B1 | 6/2004 | Schulte et al. | |
| 6,780,584 | B1 | 8/2004 | Edman et al. | |
| 6,794,197 | B1 | 9/2004 | Indermuhle et al. | |
| 6,818,184 | B2 | 11/2004 | Fulwyler et al. | |
| 6,967,251 | B2 | 11/2005 | Haugland et al. | |
| 7,110,585 | B2 | 9/2006 | Cork et al. | |
| 7,267,948 | B2 | 9/2007 | Vo-Dinh | |
| 7,736,890 | B2 | 6/2010 | Sia et al. | |
| 8,574,924 | B2 | 11/2013 | Sia et al. | |
| 2001/0002315 | A1 | 5/2001 | Schultz et al. | |
| 2002/0019059 | A1 | 2/2002 | Chow et al. | |
| 2002/0142618 | A1 | 10/2002 | Parce et al. | |
| 2002/0177144 | A1 | 11/2002 | Remacle et al. | |
| 2003/0034251 | A1 | 2/2003 | Chikarmane et al. | |
| 2003/0064507 | A1 | 4/2003 | Gallagher et al. | |
| 2003/0118486 | A1 | 6/2003 | Zhou et al. | |
| 2003/0138969 | A1 | 7/2003 | Jakobsen et al. | |
| 2003/0139886 | A1 | 7/2003 | Bodzin et al. | |
| 2003/0178641 | A1 * | 9/2003 | Blair | B01F 5/0618 257/200 |
| 2003/0207328 | A1 | 11/2003 | Yguerabide et al. | |
| 2003/0211488 | A1 | 11/2003 | Mirkin et al. | |
| 2003/0215865 | A1 | 11/2003 | Mayer et al. | |
| 2004/0014106 | A1 | 1/2004 | Patno et al. | |
| 2004/0037739 | A1 * | 2/2004 | McNeely | B01F 5/10 422/417 |
| 2004/0077074 | A1 | 4/2004 | Ackley et al. | |
| 2004/0086897 | A1 | 5/2004 | Mirkin et al. | |
| 2004/0146917 | A1 | 7/2004 | Cork et al. | |
| 2004/0191921 | A1 | 9/2004 | Farquharson et al. | |
| 2005/0059030 | A1 | 3/2005 | Bao et al. | |
| 2005/0130174 | A1 | 6/2005 | Bao et al. | |
| 2005/0141843 | A1 | 6/2005 | Warden et al. | |
| 2005/0164373 | A1 | 7/2005 | Oldham et al. | |
| 2005/0227373 | A1 * | 10/2005 | Flandre et al. | 436/518 |
| 2005/0282288 | A1 | 12/2005 | Farquharson et al. | |
| 2006/0014161 | A1 | 1/2006 | Landt et al. | |
| 2006/0014172 | A1 | 1/2006 | Muller et al. | |
| 2006/0084069 | A1 | 4/2006 | Chan et al. | |
| 2006/0147927 | A1 | 7/2006 | Geddes et al. | |
| 2007/0041624 | A1 | 2/2007 | Cork et al. | |
| 2007/0148665 | A1 | 6/2007 | Cork et al. | |
| 2007/0298433 | A1 | 12/2007 | Sia et al. | |
| 2010/0221727 | A1 | 9/2010 | Hainfeld et al. | |
| 2010/0279310 | A1 | 11/2010 | Sia et al. | |

FOREIGN PATENT DOCUMENTS

| | | | |
|---|---|---|---|
| EP | 0643307 | A1 | 3/1995 |
| EP | 928420 | B1 | 7/1999 |
| EP | 1054259 | | 11/2000 |
| EP | 1439392 | A3 | 7/2005 |
| EP | 1740951 | B1 | 1/2007 |
| EP | 1798556 | A1 | 6/2007 |
| EP | 1912067 | A1 | 4/2008 |
| EP | 1912068 | A1 | 4/2008 |
| JP | 2000-019175 | A | 1/2000 |
| JP | 2001-000197 | A | 1/2001 |
| JP | 2001-004628 | A | 1/2001 |
| JP | 2002-236131 | A | 8/2002 |
| JP | 2002-527750 | A | 8/2002 |
| JP | 2002-340897 | A | 11/2002 |
| JP | 2003-075444 | A | 3/2003 |
| JP | 2003-223674 | A | 8/2003 |
| JP | 2006-524815 | A | 11/2006 |
| JP | 2008-139296 | A | 6/2008 |
| WO | WO 91/01003 | | 1/1991 |
| WO | WO 00/22434 | A1 | 4/2000 |
| WO | WO 02/014869 | A2 | 2/2002 |
| WO | WO 03/054513 | A2 | 7/2003 |
| WO | WO 04/087951 | A2 | 10/2004 |
| WO | WO 04/087951 | A3 | 10/2004 |
| WO | WO 04/097419 | A1 | 11/2004 |
| WO | WO 2005/047864 | A2 | 5/2005 |
| WO | WO 2005/066613 | A1 | 7/2005 |
| WO | WO 2005/123966 | A2 | 12/2005 |
| WO | WO 2006/022495 | A1 | 3/2006 |

(56) References Cited

FOREIGN PATENT DOCUMENTS

| | | | |
|---|---|---|---|
| WO | WO 2006/065762 | A2 | 6/2006 |
| WO | WO 2006/116037 | A2 | 11/2006 |
| WO | WO 2006/122222 | A2 | 11/2006 |
| WO | WO 2007/047455 | A9 | 4/2007 |
| WO | WO 2007/135591 | A1 | 11/2007 |
| WO | WO 2007/135593 | A1 | 11/2007 |
| WO | WO 2008/013813 | A2 | 1/2008 |

OTHER PUBLICATIONS

International Preliminary Report on Patentability for PCT/US2004/043585 dated Jul. 13, 2006.

Ahn et al., "Disposable Smart Lab on a Chip for Point-of-Care Clinical Diagnostics," *Proceedings of the IEEE*, vol. 92, No. 1, pp. 154-173 (2004).

Andersson et al., "Micromachined flow-through filter-chamber for chemical reactions on beads," *Sensors and Actuators*, vol. B67, pp. 203-208 (2000).

Darion et al., "Chemical sensing using an integrated microfluidic system based on the Berthelot reaction," *Sensors and Actuators*, vol. B76, pp. 235-243 (2001).

Dodge et al., "Electrokinetically Driven Microfluidic Chips with Surface-Modified Chambers for Heterogeneous Immunoassays," *Anal. Chem*., vol. 73, pp. 340-3409 (2001).

Juncker et al., "Autonomous Microfluidic Capillary Systems," *Anal. Chem*, vol. 74, pp. 6139-6144 (2002).

Linder et al., Reagent-loaded cartridges for valveless and automated fluid delivery in microfluidic devices. Anal Chem. Jan. 1, 2005;77(1):64-71.

Moorthy et al., "Microfluidic tectonics platform: A colorimetric, disposable botulinum toxin enzyme-linked immunosorbent assay system," *Electrophorsis*, vol. 25, pp. 1705-1713 (2004).

Obeid et al., "Microfabricated Device for DNA and RNA Amplification by Continuous-Flow Polymerase Chain Reaction and Reverse Transcription-Polymerase Chain Reaction with Cycle Number Selection," *Anal. Chem*., vol. 75, pp. 288-295 (2003).

Proceedings of uTAS 2004, 8th International Conference on Miniaturized Systems in Chemistry and Life Sciences, Sep. 26-30, Malmo, Sweden, Edited by Thomas Laurell, Johan Nilsson, Klavs Jensen, D. Jed Harrison, Jorg P. Kutter, The Royal Society of Chemistry, pp. 1-135, 2004.

Sia et al., "An Integrated Approach to a Portable and Low-Cost Immunoassay for Resource-Poor Settings," *Angew. Chem. Int. Ed*., vol. 43, pp. 498-502 (2004).

Sia et al., "Microfluidic devices fabricated in poly(dimethlysiloxane) for biological studies," *Electrophoresis*, vol. 24, pp. 3563-3576 (Nov. 2003).

Weigle et al., "Lab-on-a-chip for drug development," *Advanced Drug Delivery Reviews*, vol. 55, pp. 349-377 (2003).

* cited by examiner

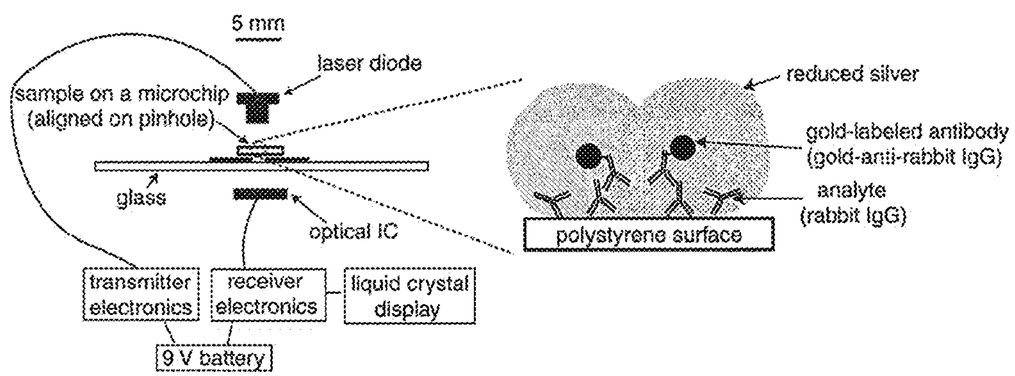
FIGURE 9A
FIGURE 9B
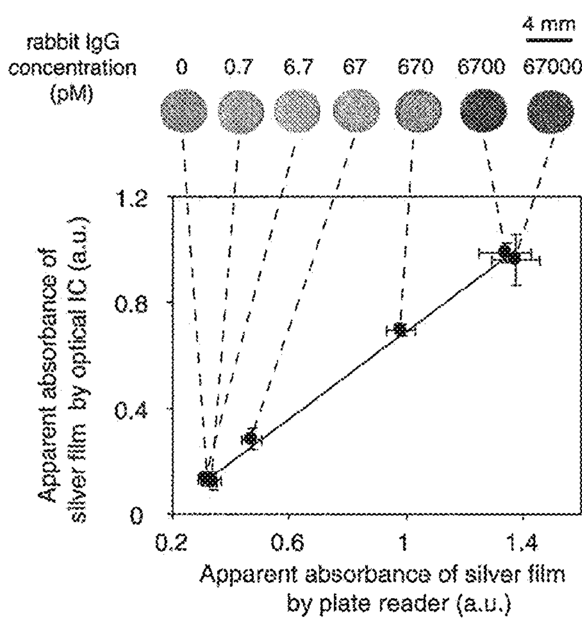
FIGURE 10

ASSAY DEVICE AND METHOD

RELATED APPLICATIONS

This application is a continuation of Ser. No. 12/769,489, filed Apr. 28, 2010, now U.S. Pat. No. 8,574,924, entitled "Assay Device and Method", which is a divisional of U.S. application Ser. No. 10/584,819 filed Jun. 14, 2007, now U.S. Pat. No. 7,736,890, entitled "Assay Device and Method", which is a U.S. National Stage application of International Patent Application Serial No. PCT/US2004/043585, filed Dec. 29, 2004, entitled "Assay Device and Method", by Sia, et al., which claims priority to U.S. Provisional Patent Application Ser. No. 60/533,627, filed Dec. 31, 2003, entitled "Assay Device and Method", by Sia, et al., and to U.S. Provisional Patent Application Ser. No. 60/539,416, filed Jan. 26, 2004, entitled "Assay Device and Method", by Sia, et al., each of which is incorporated herein by reference in its entirety.

FEDERALLY SPONSORED RESEARCH

This invention was sponsored by National Institute of Health grant GM30367 and National Science Foundation grant ECS-9729405. The Government has certain rights in the invention.

BACKGROUND OF INVENTION

1. Field of Invention

This invention relates to a method and apparatus for determining an analyte and, in particular, to the determination of an analyte indicating a disease condition.

2. Background of the Invention

An accurate early and ongoing determination of a disease condition is important for the prevention and treatment of human and animal diseases. One class of diagnostic techniques uses immunoassay reactions to detect the presence of either an antigen or an antibody in a sample taken from a subject. These immunoassay methods include, for example, ELISA, immunochromatographic assays (strip tests, dipstick assays and lateral flow assays), and sandwich assays. Accuracy, reliability, and ease of use of these types of assays has improved, but often testing requires laboratory conditions, power supplies, and training that may not be available in some areas where testing is desired.

One type of sandwich assay uses gold-conjugated antibodies to enhance detection. For example, see PCT publication WO/91/01003. Enhancement of a gold colloid signal can be achieved by staining the gold colloids with silver. First, in the case of HIV, an HIV antigen is immobilized onto a solid polystyrene substrate. A human anti-HIV antibody is then captured by the antigen and is therefore itself immobilized on the substrate. The antibody is then exposed to anti-human IgG labeled with a colloidal gold particle and thus labeled IgG becomes bonded to the antibody. The antigen-antibody-IgG complex is then exposed to a solution containing silver ions and these become nucleated around the gold particles as solid silver particles having a dark color to the eye.

The development of microfluidics and microfluidic techniques has provided improved chemical and biological research tools, including platforms for performing chemical reactions, combining and separating fluids, diluting samples, and generating gradients. For example, see U.S. Pat. No. 6,645,432, hereby incorporated by reference herein.

SUMMARY OF INVENTION

This invention relates to a method and apparatus for determining an analyte and, in particular, to the determination of an analyte indicating a disease condition.

In one embodiment, the present invention is directed to a method comprising accumulating an opaque material on a region of a microfluidic chamber, exposing the region to light, and determining the transmission of light through the opaque material.

In another embodiment, the present invention is directed to an immunoassay comprising a microfluidic chamber having a surface, at least one of an antigen or an antibody disposed on a portion of the chamber surface, and an opaque layer associated with the portion of the chamber.

In another embodiment, the present invention is directed to a method comprising passing a fluid sample over a surface, allowing a sample component to bind with a binding partner disposed on the surface, allowing a metal colloid to associate with a sample component, and flowing a metal solution over the surface to form a metallic layer.

In another embodiment, the present invention is directed to a method comprising flowing a fluid sample over a surface, allowing a sample component to bind with a binding partner disposed on the surface, and accumulating an opaque material on a portion of the surface.

In another embodiment, the present invention is directed to an assay kit comprising a surface including a microfluidic channel, at least one of an antibody or an antigen associated with a portion of the microfluidic channel, a metal colloid associated with an antibody or an antigen, a metal precursor, and instructions for performing the assay.

In yet another embodiment, the present invention is directed to a method comprising contacting a sample with an antibody or an antigen, allowing a sample component to bind with the antibody or antigen, illuminating any bound sample component with a pulse modulated light, and determining binding of a sample component to an antigen or antibody.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component is labeled in every drawing. In the drawings:

FIG. 9*a* provides a side view of an assay detection system;

FIG. 9*b* provides a side view of a detection area of an assay;

FIG. 10 provides graphical data comparing apparent absorbance by two different techniques;

DETAILED DESCRIPTION

Figure 1:
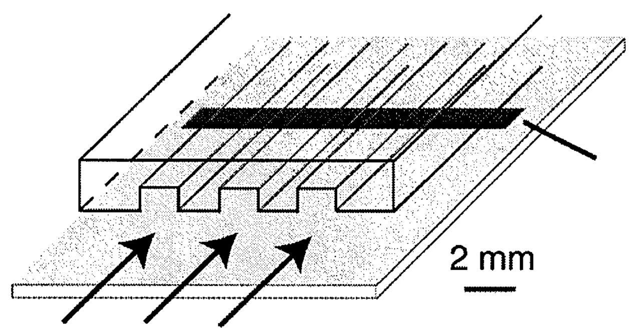
FIG. 1 is an illustration of one embodiment of an assay of the invention.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

The invention provides a method and apparatus for determining a presence, qualitatively or quantitatively, of a component in a sample. The component may be a binding partner, such as an antibody or antigen, that may be indicative of a disease condition.

In one aspect, a sample from a subject can be analyzed with little or no sample preparation. The sample may also be obtained non-invasively, thus providing for a safer and more patient-friendly analytical procedure.

In another aspect, an assay providing high sensitivity and a low limit of detection, comparable to that of the most sensitive ELISA test, is provided. The assay can be run quickly and results may be permanent, allowing for reading the assay at any time after performing the test.

In another aspect, a sample is flowed over a surface associated with a prospective binding partner of a sample component. The assay can be performed in a channel of a microfluidic device allowing the sample to be flowed over a binding partner, for example, an antigen. Any antigen-antibody complex that forms may be associated with a metal colloid that provides a catalytic surface for the deposition of an opaque material, such as a layer of metal. Therefore, if antibody-antigen binding occurs in the microfluidic channel, the flowing of a metal precursor through the channel can result in the formation of an opaque layer, such as a silver layer, due to the presence of the catalytic metal colloid associated with the antibody-antigen complex. Any opaque layer that is formed in the microfluidic channel can be detected optically, for example, by measuring a reduction in light transmittance through a portion of the microfluidic channel compared to a portion of the channel that does not include the antibody or antigen. The opaque layer may provide an increase in assay sensitivity when compared to techniques that do not form an opaque layer.

The term "binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

An "opaque material" is a substance that interferes with the transmittance of light at one or more wavelengths. An opaque material does not merely refract light, but reduces the amount of transmission through the material by, for example, absorbing or reflecting light. Different opaque materials or different amounts of an opaque material may allow transmittance of less than 90, 80, 70, 60, 50, 40, 30, 20, 10 or 1 percent of the light illuminating the opaque material. Examples of opaque materials include molecular layers of elemental metal and polymeric layers.

The term "binding partner" refers to a molecule that can undergo binding with a particular molecule. Biological binding partners are examples. For instance, Protein A is a binding partner of the biological molecule IgG, and vice versa. Likewise, an antibody is a binding partner to its antigen, and vice versa.

"Colloids", as used herein, means nanoparticles, i.e., very small, self-suspendable or fluid-suspendable particles including those made of material that is, e.g., inorganic or organic, polymeric, ceramic, semiconductor, metallic (e.g., gold), non-metallic, crystalline, amorphous, or a combination. Typically, colloid particles used in accordance with the invention are of less than 250 nm cross section in any dimension, more typically less than 100 nm cross section in any dimension, and in most cases are of about 2-30 nm cross section. One class of colloids suitable for use in the invention is 10-30 nm in cross section, and another about 2-10 nm in cross section. Colloids may be associated with a binding partner, for example, an antibody. As used herein this term includes the definition commonly used in the field of biochemistry.

As used herein, a component that is "immobilized relative to" another component either is fastened to the other component or is indirectly fastened to the other component, e.g., by being fastened to a third component to which the other component also is fastened, or otherwise is transitionally associated with the other component. For example, a signaling entity is immobilized with respect to a binding species if the signaling entity is fastened to the binding species, is fastened to a colloid particle to which the binding species is fastened, is fastened to a dendrimer or polymer to which the binding species is fastened, etc.

"Signaling entity" means an entity that is capable of indicating its existence in a particular sample or at a particular location. Signaling entities of the invention can be those that are identifiable by the unaided human eye, those that may be invisible in isolation but may be detectable by the unaided human eye if in sufficient quantity (e.g., colloid particles), entities that absorb or emit electromagnetic radiation at a level or within a wavelength range such that they can be readily detected visibly (unaided or with a microscope including an electron microscope or the like), optically, or spectroscopically, entities that can be detected electronically or electrochemically, such as redox-active molecules exhibiting a characteristic oxidation/reduction pattern upon exposure to appropriate activation energy ("electronic signaling entities"), or the like. Examples include dyes, pigments, electroactive molecules such as redox-active molecules, fluorescent moieties (including, by definition, phosphorescent moieties), up-regulating phosphors, chemiluminescent entities, electrochemiluminescent entities, or enzyme-linked signaling moieties including horseradish peroxidase and alkaline phosphatase. "Precursors of signaling entities" are entities that, by themselves, may not have signaling capability but, upon chemical, electrochemical, electrical, magnetic, or physical interaction with another species, become signaling entities. An example includes a chromophore having the ability to emit radiation within a particular, detectable wavelength only upon chemical interaction with another molecule. Precursors of signaling entities are distinguishable from, but are included within the definition of, "signaling entities" as used herein.

In some, but not all embodiments, all components of the systems and methods described herein are microfluidic. "Microfluidic," as used herein, refers to a device, apparatus or system including at least one fluid channel having a cross-sectional dimension of less than 1 mm, and a ratio of length to largest cross-sectional dimension of at least 3:1. A "microfluidic channel," as used herein, is a channel meeting these criteria.

The "cross-sectional dimension" of the channel is measured perpendicular to the direction of fluid flow. Most fluid channels in components of the invention have maximum cross-sectional dimensions less than 2 mm, and in some cases, less than 1 mm. In one set of embodiments, all fluid channels containing embodiments of the invention are microfluidic or have a largest cross sectional dimension of no more than 2 mm or 1 mm. In another embodiment, the fluid channels may be formed in part by a single component (e.g., an etched substrate or molded unit). Of course, larger channels, tubes, chambers, reservoirs, etc. can be used to store fluids in bulk and to deliver fluids to components of the invention. In one set of embodiments, the maximum cross-sectional dimension of the channel(s) containing embodiments of the invention are less than 500 microns, less than 200 microns, less than 100 microns, less than 50 microns, or less than 25 microns.

A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

As used herein, "fastened to or adapted to be fastened", in the context of a species relative to another species or to a surface of an article, means that the species is chemically or biochemically linked via covalent attachment, attachment via specific biological binding (e.g., biotin/streptavidin), coordinative bonding such as chelate/metal binding, or the like. For example, "fastened" in this context includes multiple chemical linkages, multiple chemical/biological linkages, etc., including, but not limited to, a binding species such as a peptide synthesized on a polystyrene bead, a binding species specifically biologically coupled to an antibody which is bound to a protein such as protein A, which is attached to a bead, a binding species that forms a part (via genetic engineering) of a molecule such as GST or Phage, which in turn is specifically biologically bound to a binding partner covalently fastened to a surface (e.g., glutathione in the case of GST), etc. As another example, a moiety covalently linked to a thiol is adapted to be fastened to a gold surface since thiols bind gold covalently. Similarly, a species carrying a metal binding tag is adapted to be fastened to a surface that carries a molecule covalently attached to the surface (such as thiol/gold binding) which molecule also presents a chelate coordinating a metal. A species also is adapted to be fastened to a surface if a surface carries a particular nucleotide sequence, and the species includes a complementary nucleotide sequence.

A microfluidic device of the invention can be fabricated of a polymer, for example an elastomeric material such as poly(dimethylsiloxane) (PDMS) using rapid prototyping and soft lithography. For example, a high resolution laser printer may be used to generate a mask from a CAD file that represents the channels that make up the fluidic network. The mask may be a transparency that may be contacted with a photoresist, for example, SU-8 photoresist (MicroChem), to produce a negative master of the photoresist on a silicon wafer. A positive replica of PDMS may be made by molding the PDMS against the master, a technique known to those skilled in the art. To complete the fluidic network, a flat substrate, for example, a glass slide, silicon wafer, or polystyrene surface may be placed against the PDMS surface and may be held in place by van der Waals forces, or may be fixed to the PDMS using an adhesive. To allow for the introduction and receiving of fluids to and from the network, holes (for example 1 millimeter in diameter) may be formed in the PDMS by using an appropriately sized needle. To allow the fluidic network to communicate with a fluid source, tubing, for example of polyethylene, may be sealed in communication with the holes to form a fluidic connection. To prevent leakage, the connection may be sealed with a sealant or adhesive such as epoxy glue.

In one embodiment, as shown in FIG. 1, a microfluidic device 110 can be used to provide a substrate on which to perform the assay. Methods of manufacturing such a microfluidic device are provided in U.S. Pat. No. 6,645,432, incorporated by reference in its entirety herein.

A series of microfluidic channels, 120, 122, and 124, can be used to flow sample and metal precursor across the surface 130 of the microfluidic device. A binding partner, for example, an antigen or antibody, may be disposed on surface 130 at portion 140. Portion 140 may include a stripe of binding partner, as shown, transversing two or more channels. Alternatively, a binding partner may be disposed on a portion limited to a single channel. Multiple binding partners may be disposed in a single channel and may overlap or be segregated from each other.

Binding partners immobilized at a region or portion of a region can be immobilized in essentially any manner, and many immobilization techniques suitable for use with the invention are known in the art. See U.S. patent application Ser. Nos. 10/654,587 and 09/578,562, which are incorporated by reference in their entirety herein. Immobilization can be done in a way such that the species are randomly oriented relative to the surface (i.e., each immobilized species can be oriented, relative to the surface, randomly), or greater control of the orientation of species relative to the surface can be provided. For example, where proteins are immobilized at the surface, they can be oriented such that their binding sites for the assay are oriented generally away from the surface, maximizing their binding capacity or availability. One technique for doing so, described in U.S. Pat. No. 5,620,850, incorporated herein by reference, involves synthesizing the protein with a polyamino acid tag such as, for example, a sequence of 6 histidines, at a location generally opposite the protein's relevant binding site, providing a metal chelate, such as nitrilotriacetic acid, chelating a metal ion such as nickel in such a way that at least two coordination sites on nickel are free for binding to the polyamino acid tag, and allowing the tag to coordinate to the metal ions, thus immobilizing the protein at the region or portion of a region in an advantageous orientation. A metal chelate such as this can be immobilized at the region in any of a number of ways. One way involves forming a self-assembled monolayer (SAM) at the region, terminating in the metal chelate, as described in the above-referenced U.S. Pat. No. 5,620,850. For example, a thin, essentially transparent thin gold layer can be deposited at the region, and SAM-forming alkyl thiols, terminating in a metal chelate, can be deposited on the gold layer as a SAM. Other chemistry, described in U.S. Pat. No. 5,620,850 and other references, and known to those of ordinary skill in the art, can be used to form such a SAM on a region defined by a variety of base materials.

To run the assay, a sample, such as a biological sample taken from a subject, is flowed through one or more microchannels 120, 122, or 124, in the direction shown by the arrows. The sample may be a liquid sample, but in some embodiments need not be diluted, purified or treated prior to analysis. The sample may be flowed through the microchannel at a rate sufficient to allow a component of the sample to bind with a binding partner immobilized at portion 140. By actively flowing the sample through the channel, the reactive portion 140 is repeatedly exposed to components of the sample, improving reaction kinetics and resulting in an increased formation of any binding pairs. After an adequate amount of flow of sample through microchannel 120, e.g., when detectable binding pairs have formed, a fluid containing a metal colloid associated with a second binding partner of the sample component is flowed through the microchannel, allowing the metal colloid to bind with any sample component that has been associated with portion 140 of the microchannel.

After the metal colloid has been given the opportunity to bind with any binding partner at portion 140, a metal precursor can be flowed through channel 120 in a similar manner as was the metal colloid. The metal precursor can be flowed through the microchannel at a concentration and a rate that allows an opaque layer to be formed wherever a threshold number of metal colloids have been associated with the surface. Thus, if a gold-conjugated antibody is used as a metal colloid, a silver nitrate solution may be used to electrolessly deposit a silver layer on the portion of the channel associated with the gold-conjugated antibody. At the completion of this portion of the assay, surface 130 of the microfluidic network may include, in successive layers, an antigen such as HIV antigen, a sample component of an HIV antibody obtained from a subject, a metal colloid such as gold-labeled anti-human IgG, and an opaque layer of metal, such as silver, that has been electrolessly deposited on the metal colloid. Rinsing solutions may be flowed through the channel before or after each of the steps.

In addition to depositing metal on any metal colloids that may be associated with portion 140 of microchannel 120, the metal precursor may also be deposited on metal that has previously been electrolessly deposited on the gold-conjugated antibody. In this manner, an opaque material may be formed over some or all of portion 140 allowing for detection by, for example, the unaided eye or an optical detection device. The opaque material may be a continuous material rather than, for example, independent particles, and may include a horizontal dimension that, in a dimension measured in substantially the same plane as surface 130, measures greater than 1 micron, greater than 10 microns, or greater than 100 microns.

In some cases, an opaque layer may form a web or honeycomb of material that includes passages allowing light to be transmitted therethrough. As additional material is deposited, these passages may become smaller, allowing less and less light to be transmitted through the material. As the passages disappear, the amount of light transmittance may be reduced to zero, providing for a completely opaque material.

Figure 2:
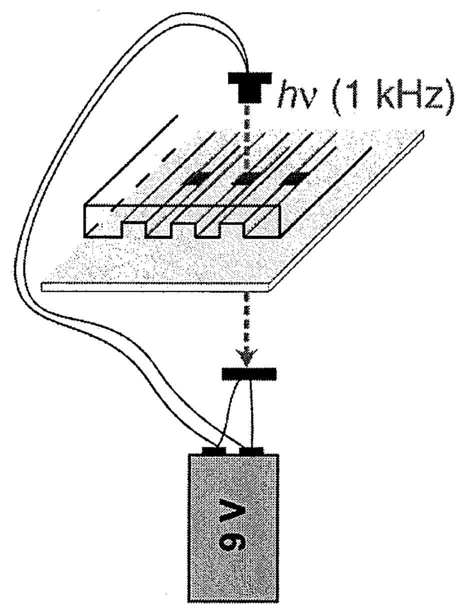
FIG. 2 is an illustration of an assay including a detector.
Figure 3:
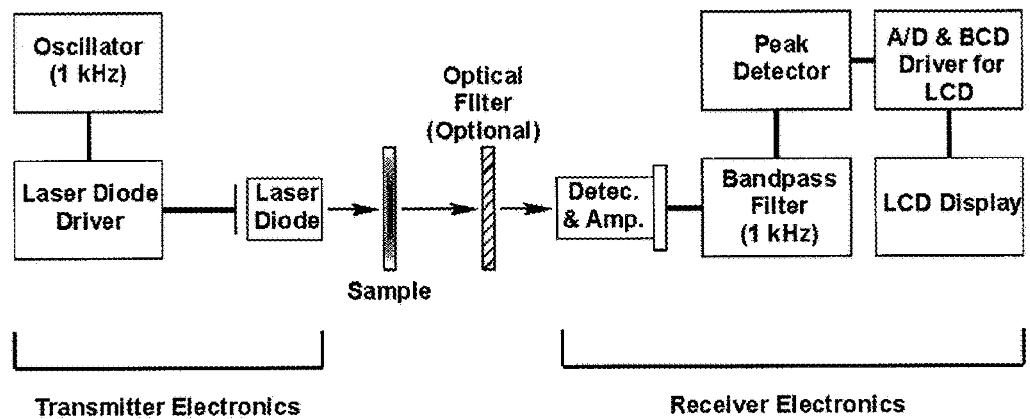
FIG. 3 is a schematic illustration of an optical detector.

After an opaque layer has been formed, detection of the opaque layer, and therefore determination of the presence of a binding partner, may be determined by visually examining the microfluidic device or by using a detector such as an optical detector. One embodiment of an optical detector is depicted in FIGS. 2, 3 and 9. FIG. 2 illustrates microfluidic device 110, as shown in FIG. 1. Also included is light source 210, here an oscillator-modulated laser diode, and a detector 220, such as an optical integrated circuit (IC). As illustrated in the schematic diagram of FIG. 3, the detector signal may be amplified and passed through a bandpass filter centered at the same frequency as the oscillator controlling the light source. The output may then be passed to an A/D converter which can then provide an output on a readout, such as an LCD display. Both the light source and the detector may be powered by a 9 volt battery, such as the type typically used in portable hand-held radios.

In one aspect, the invention provides an apparatus and method for analyzing a sample using continuous flow. Typically, existing methods such as ELISA and other sandwich assays use a 96 well plate, or similar, for containing a sample for the immunoassay. These methods can expose an antibody or an antigen to a sample component in a fluid, but the fluid is not flowed past the antibody or antigen and diffusion is relied on for bringing binding partners into proximity with each other. The present invention may allow for increased opportunities for binding of a sample component to a potential binding partner at similar or lower concentrations of sample component than previous methods. By flowing a sample containing one binding partner past a surface presenting the other binding partner, a greater number of potential binding partners are placed in proximity to each other than would occur via simple diffusion. In one embodiment, the sample is flowed through a microchannel providing the benefits of flowing one binding partner past a second binding partner while requiring a small sample, for example, less than 10 microliters, less than 1 microliter, or less than 100 nanoliters of sample. The microchannel may be of a material transparent to light that is used to detect the formation of an opaque material in the channel so that any absorbance or transmittance of light through a portion of the channel can be attributed to the formation of an opaque layer.

Because immunoassays detect signaling entities, such as enzyme-conjugated secondary antibodies that are dissolved or suspended in a fluid, a relatively long path length is required in order to obtain optimal sensitivity. Thus, one reason why immunoassays have not been applied in microfluidics is the short path length typically presented by microfluidic devices. For example, a microfluidic device may have a channel having a thickness of less than 250 microns, less than 100 microns, or less than 40 microns. Therefore, any fluid filling a channel in this microfluidic device would present a perpendicular light pathway of less than 250, 100 or 40 microns. The present method may not be subject to these restrictions because it can use an opaque layer in the solid state, rather than a chromophore in a fluid. The opaque layer may have a thickness of less than 1 micron, of less than 100 nanometers or less than 10 nanometers. Even at these small thicknesses, a detectable change in transmittance can be obtained.

The geometry of the microfluidic channel may provide for the laminar flow of fluids through the channel, even at relatively high flow rates. Alternatively, turbulent flow may be employed for example, by using even faster flow rates, wider channels, or devices such as microfluidic mixers. Such mixing may provide for a greater amount of contact between potential binding partners.

The presence, absence, or amount of an analyte in a sample may be indicated by the formation of an opaque material. Although the opaque material may be used to refract light or may be excited to emit light at a similar or different wavelength than the light to which the layer is exposed, the measurement of light transmission may be preferred due to, for example, lower equipment and operating costs, and ease of use. In some microchannels, an opaque layer may be visible to the naked eye and, in particular if reflective, may be detected without the use of instrumentation.

Any opaque material that forms can be a series of discontinuous independent particles, but in one embodiment is a continuous material that takes on a generally planar shape. The opaque material may have a dimension greater than 1 micron or greater than 10 microns. The opaque material may be a metal and is preferably a metal that can be electrolessly deposited. These metals include, for example, copper, nickel, cobalt, palladium, and platinum. A metal precursor is a material that can provide the source of the elemental metal for depositing on, for example, a metal colloid. For example, a metal precursor may be a metallic salt solution such as silver nitrate. In one embodiment, a metal precursor may include 0.1% silver nitrate, 1.7% hydroquinone and 0.1 M citrate buffer at a pH of 3.5. Some other examples of electrolessly deposited materials can be found in Modern Electroplating, $4^{th}$ Edition, Schlesinger and Paunovic, Wiley, 2000. Metal precursors can be stored for long periods of time and may be stable for several years whereas optically-active compounds may have much shorter shelf lives.

Any metal colloid associated with a surface may be widely scattered over a portion of the surface. For example, gold-conjugated antibodies may be bound to sample components that are associated with the portion of the surface but spaces may exist between the gold-conjugated antibodies, making them discontinuous. When a metal precursor is first exposed to these gold-conjugated antibodies, the precursor may form particulates centered around individual metal colloids. As metal, e.g., silver, is deposited on these metal colloids, the particles become larger and soon the metal precursor may deposit metal not only on gold colloids but on metal that has been previously electrolessly deposited. For example, a silver nitrate solution may deposit silver metal onto silver metal particles that have previously been deposited on gold-conjugated antibodies. Thus, as the silver layer continues to grow on silver, as well as on gold, areas that previously were independent particles or islands of metal can join to form a larger, continuous opaque material that can be more easily detected. It has been found that a microfluidic system can provide for a relatively smooth, continuous layer of metal. The opaque material may have a thickness greater than 1, 10, 100 or 1000 nanometers. For some opaque materials, the material may become completely opaque at thicknesses greater than about 100 nm. However, in some embodiments, such as when a honeycomb or similar structure is formed, thicknesses in some portions may be much greater while still allowing some light to be transmitted.

A variety of chemical and biological materials may be analyzed by the methods and apparatuses described herein. Analytes may include chemicals such as organic compounds and biological materials such as proteins, peptides, nucleic acids and antibodies.

Analytes include any analyte for which a binding partner can be found. Analytes that may be determined include specific proteins, viruses, hormones, drugs, nucleic acids and polysaccharides; specifically antibodies, e.g.: IgD, IgG, IgM or IgA immunoglobulins to HTLV-I, HIV, Hepatitis A, B and non A/non B, Rubella, Measles, Human Parvovirus B19, Mumps, Malaria, Chicken Pox or Leukemia; human and animal hormones, e.g.: human growth hormone (hGM, human chorionic gonadotropin WM; drugs, e.g.: paracetamol or theophylline; marker nucleic acids, e.g.; as for genetic finger printing analysis markers; polysaccharides such as cell surface antigens for HLA tissue typing and bacterial cell wall material. Chemicals that may be detected include explosives such as TNT, nerve agents, and environmentally hazardous compounds such as polychlorinated biphenyls (PCBs), dioxins, hydrocarbons and MTBE. Typical sample fluids include physiological fluids such as human or animal whole blood, blood serum, blood plasma, semen, tears, urine, sweat, saliva, cerebro-spinal fluid, and vaginal secretions, in-vitro fluids used in research, or environmental fluids such as aqueous liquids suspected of being contaminated by the analyte.

In cases where an antigen is being analyzed, a corresponding antibody can be the binding partner associated with a surface of a microfluidic channel. If an antibody is the analyte, then an appropriate antigen may be the binding partner associated with the surface. When a disease condition is being determined, it may be preferred to put the antigen on the surface and to test for an antibody that has been produced in the subject. Such antibodies may include, for example, antibodies to HIV.

A biological sample may be obtained noninvasively. The low level of detection capable with the invention allows for the use of samples that typically contain lower concentrations of antigens or antibodies than does blood. For example, useful samples may be obtained from saliva, urine, sweat, or mucus. By allowing samples to be obtained noninvasively, the methods of the invention can provide for increased throughput, safer sampling, and less subject apprehension.

Figure 4:
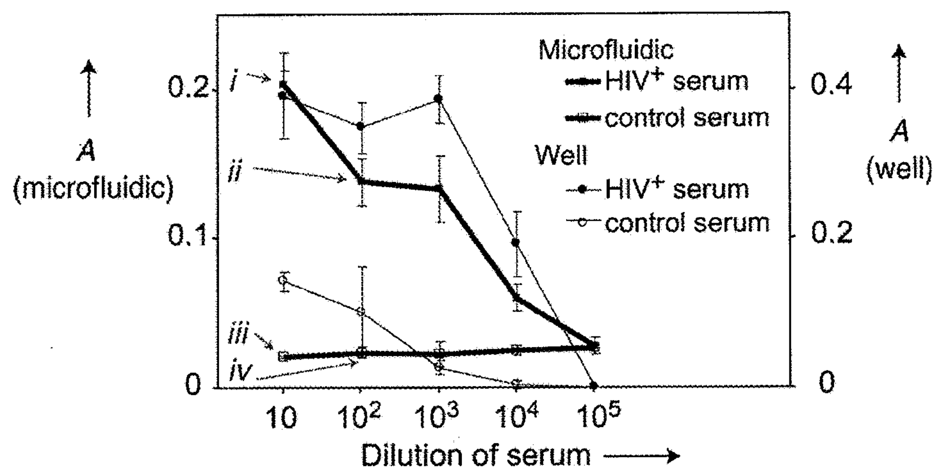
FIG. 4 is a graph illustrating absorbance versus analyte concentration.
Figure 5:
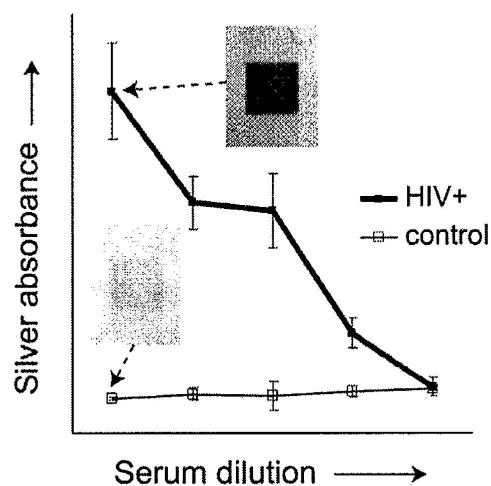
FIG. 5 illustrates graphically and in a photocopy of a micrograph the amount of opaque material present at high and low analyte concentrations.
Figure 6:
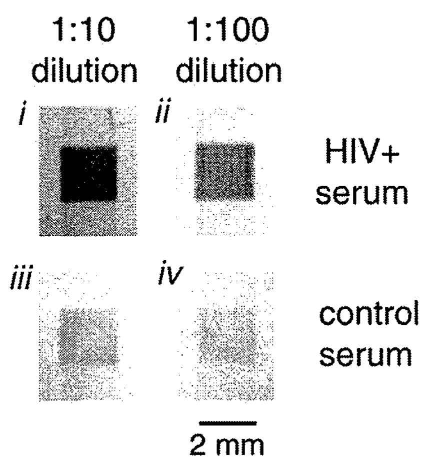
FIG. 6 provides photocopies of micrographs showing the formation of opaque material at various analyte concentrations.

The methods and apparatuses of the present invention may be capable of obtaining limits of detection (LOD) comparable to those achievable by immunochromatographic assays as well as ELISA. For example, concentrations below 1 nM and even in the 100 pM range can be detected. The assay can be qualitative, quantitative, or both. As illustrated in FIG. 4, as the concentration of analyte increases, the apparent absorbance of the opaque material increases accordingly. In FIG. 4, the sample component (analyte) is HIV antigen and the sample is human serum. Different dilutions of these sera are shown and in FIG. 6 the formation of an opaque layer indicates a positive result when compared to control at dilutions of 1 to 10 and 1 to 100. Therefore, in addition to presence/absence type tests, a quantitative test may be provided. Such a quantitative test may be of interest, for example, to those monitoring antibody levels in a patient during treatment.

Sensitivity and LOD of the method compare favorably to that obtainable with various state-of-art ELISA techniques. When compared to ELISA techniques using chemiluminescence, fluorescence and absorbance in assaying rabbit IgG, an embodiment of the invention using silver deposition provided comparable sensitivity and LOD numbers. Sensitivity and LOD were calculated using IUPAC definitions and are provided in Table 1 below. Higher sensitivity numbers indicate greater sensitivity and lower LOD numbers indicate a lower LOD.

TABLE 1

| Method | Sensitivity (normalized) | LOD (pM) |
|---|---|---|
| Silver deposition | .08 | 89 |
| Chemiluminescence | .19 | 22 |
| Fluorescence | .12 | 163 |
| Absorbance | .04 | 55 |

In another embodiment, an assay is provided that requires less time to run than typical immuno-based assays such as ELISA. For example, using a microfluidic device of the present invention, incubation times for each reagent can be less than 10 minutes. For ELISA techniques using microwells, 1 to 3 hours incubation time is typically required for each reagent. Thus, the present method can provide a 6 to 18 fold decrease in incubation time. A portion of this time savings can be attributed to analyzing a sample directly without needing to purify, dilute or otherwise prepare a sample. For example, a saliva sample may be flowed across a channel without having been diluted, filtered, separated, or otherwise prepared. From the time a sample is obtained to when results are realized, a total time of less than one hour, less than 30 minutes, less than 20 minutes or less than 10 minutes may be realized. One reason for this increase in speed is an improved rate of binding between binding partners. This can be attributed, at least in part, to the flow system of the invention. Systems relying on diffusion, or capillary action are limited in the number of binding partners that can be exposed to each other over a given time period. Furthermore, as diffusion may be temperature dependent, the present invention, utilizing sample flow, may be more temperature independent than other methods, providing for a more robust assay in the field where temperatures may vary from above 40° C. to below 0° C.

In another embodiment, two or more parallel assays may be run. A single sample may be physically split into two or more samples using a microfluidic device. A microfluidic device may have a single input channel that branches into two, three, or more parallel channels. Parallel analysis may be performed at different threshold levels of a similar or identical analyte, or for different analytes at the same or different thresholds. A control may also be performed in parallel. Thus, with a single sample run, a sample can be analyzed for two or more analytes at any number of threshold concentrations. A control may also be run concurrently and may be useful in calibrating and/or verifying the detection method that is used. Once an opaque layer is formed, the assay may be stable for an extended period of time, for example, greater than one month or one year, so that assays may be collected and analyzed or re-analyzed at a later date.

Reagents and samples may be supplied to the assay using methods known to those skilled in the art or by using delivery methods described herein.

In one aspect, a microfluidic device can be used in conjunction with a vessel designed to contain, store, protect and/or transport two or more fluids. As used herein, vessels include cartridges and tubes. A vessel may contain two or more distinct fluids separated by a third fluid that can be immiscible with both. Any number of distinct fluids may be contained in a vessel. For example, the vessel may be a tube that includes a series of fluid plugs such as a reagent solution plug followed by an air plug, followed by a rinse solution plug. An additional air plug may separate the first rinse solution plug from a second rinse solution plug. The ends of the tube may be sealed, for example, to retain the fluid plugs and to prevent contamination from external sources. The liquid plugs may retain their relative positions in the tube and may be prevented from contacting each other by the interspaced air plugs. The tube dimensions and materials of construction may be chosen to help fluid plugs retain their position and remain unmixed. For example, see the cartridge systems described in Vincent Linder, Samuel K. Sia, and George M. Whitesides "Reagent-Loaded Cartridges for Valveless and Automated Fluid Delivery in Microfluidic Devices," Anal. Chem.; 2005; 77(1) pp 64-71.

Reagents and other fluids may be stored for extended lengths of time in the vessel. For example, reagents may be stored for greater than 1 day, 1 week, 1 month or 1 year. By preventing contact between fluids, fluids containing components that would typically react or bind with each other are prevented from doing so, while being maintained in a continuous chamber.

Fluids may be transferred from the vessel to the assay by applying pressure or vacuum after removing or piercing a seal at an end of the tube. In other embodiments, the vessel need not be sealed and fluid flow can be started by applying an external force, such as a pressure differential. One end of the vessel, for example, can be in, or can be placed in, fluid communication with an assay or another device that will receive the fluids from the vessel.

Fluid may be flowed to the reaction site by, for example, pushing or pulling the fluid through the vessel. Fluids can be pushed to the reaction site using, for example, a pump, syringe, pressurized vessel, or any other source of pressure.

Alternatively, fluids can be pulled to the reaction site by application of vacuum or reduced pressure on a downstream side of the reaction site. Vacuum may be provided by any source capable of providing a lower pressure condition than exists upstream of the reaction site. Such sources may include vacuum pumps, venturis, syringes and evacuated containers.

In one set of embodiments, a vessel may contain fluid plugs in linear order so that as fluids flow from the vessel to a reaction site they are delivered in a predetermined sequence. For example, an assay may receive, in series, an antibody fluid, a rinse fluid, a labeled-antibody fluid and a rinse fluid. By maintaining an immiscible fluid (a separation fluid) between each of these assay fluids, the assay fluids can be delivered in sequence from a single vessel while avoiding contact between any of the assay fluids. Any immiscible fluid that can separate assay fluids may be applied to the reaction site without altering the conditions of the reaction site. For instance, if antibody-antigen binding has occurred at a reaction site, air can be applied to the site with minimal or no effect on any binding that has occurred.

Pre-filling of the vessel with reagents may allow the reagents to be dispensed in a predetermined order for a downstream process. In cases where a predetermined time of exposure to a reagent is desired, the amount of each fluid in the vessel may be proportional to the amount of time the reagent is exposed to a downstream reaction site. For example, if the desired exposure time for a first reagent is twice the desired exposure time for a second reagent, the volume of the first reagent in the vessel may be twice the volume of the second reagent in the vessel. If a constant pressure differential is applied in flowing the reagents from the vessel to the reaction site, and if the viscosity of the fluids is the same or similar, the exposure time of each fluid at a specific point, such as a reaction site, may be proportional to the relative volume of the fluid. Factors such as vessel geometry, pressure or viscosity can also be altered to change flow rates of specific fluids from the vessel.

A variety of determination techniques may be used. Determination techniques may include optically-based techniques such as light transmission, light absorbance, light scattering, light reflection and visual techniques. Determination techniques may also measure conductivity. For example, microelectrodes placed at opposite ends of a portion of a microfluidic channel may be used to measure the deposition of a conductive material, for example an electrolessly deposited metal. As a greater number of individual particles of metal grow and contact each other, conductivity may increase and provide an indication of the amount of conductor material, e.g., metal, that has been deposited on the portion. Therefore, conductivity or resistance may be used as a quantitative measure of analyte concentration.

Another analytical technique may include measuring a changing concentration of a precursor from the time the precursor enters the microfluidic channel until the time the precursor exits the channel. For example, if a silver nitrate solution is used, a silver sensitive electrode may be capable of measuring a loss in silver concentration due to the deposition of silver in a channel as the precursor passes through the channel.

Different optical detection techniques provide a number of options for determining assay results. In some embodiments, the measurement of transmission or absorbance means that light can be detected at the same wavelength at which it is emitted from a light source. Although the light source can be a narrow band source emitting at a single wavelength, it may also may be a broad spectrum source, emitting over a range of wavelengths, as many opaque materials can effectively block a wide range of wavelengths. The system may be operated with a minimum of optical components. For instance, the determining device may be free of a photo multiplier, may be free of a wavelength selector such as a grating, prism or filter, or may be free of a device to direct or columnate light such as a columnator. Elimination or reduction of these features can result in a less expensive, more robust device.

In some embodiments, fewer than 3, fewer than 2, or fewer than 1 optical component may be used. The term "optical component" can include passive elements or devices that do not produce electromagnetic radiation but rather diffract or refract or otherwise change a property of electromagnetic radiation or light. Thus, an optical component can, for example, be a prism, a mirror, a diffractive lens, a refractive lens, reflective lens, a spherically-shaped lens, an aspherically-shaped lens, a non-spherically-shaped lens, a plano-convex-shaped lens, a polygonal convex-shaped lens or a graded-index optical fiber or fiber optical component. An "optical component" also includes active elements or devices that produce electromagnetic radiation including, for example, lasers or light-emitting diodes. A "light-focusing element" is an optical element that is capable of refracting, bending or changing the direction of the propagating of waves of electromagnetic radiation so that the waves can converge, or diverge, on or near a preferred plane, location or region.

In one embodiment, a light source can be pulse modulated, for example, at a frequency of 1,000 Hz. To match the pulse modulated light source, a detector may include a filter operating at the same frequency. By using a pulse modulated light source it has been found that the system can be less sensitive to extrinsic sources of light. Therefore, the assay may run under various light conditions, including broad daylight, that might make it impractical to use existing techniques. Experimental results indicate that by using a pulse modulated light source and filter, results are consistent regardless of the light conditions under which the test is run.

The light source may be a laser diode. For example, an InGaAlP red semiconductor laser diode emitting at 654 nm may be used. The photodetector may be any device capable of detecting the transmission of light that is emitted by the light source. One type of photodetector is an optical integrated circuit including a photodiode having a peak sensitivity at 700 nm, an amplifier and a voltage regulator. If the light source is pulse modulated, the photodetector may include a filter to remove the effect of light that is not at the selected frequency.

EXAMPLES

Example 1

To compare a method of the invention with existing methods, an experiment was designed to assay HIV antibodies using the present method as well as ELISA techniques employing chemiluminescence, fluorescence and absorbance. Procedures and results are described below.

Reagents and equipment were obtained as follows. Rabbit IgG, anti-rabbit IgG (horseradish peroxidase conjugated), anti-rabbit IgG (alkaline phosphatase conjugated), anti-rabbit IgG (gold conjugated), p-nitrophenylphosphate (pNPP), and the silver enhancement kit were obtained from Sigma-Aldrich (St. Louis, Mo.). AttoPhos was purchased from Promega Corp. (Milwaukee Wis.). SuperSignal ELISA Femto Max was purchased from Pierce (Rockford, Ill.).

BluePhos phosphatase substrate was purchased from KPL (Gaithersburg, Md.). HIV Env antigen (gp41) was purchased from Research Diagnostics (Flanders, N.J.). HIV positive serum and control serum were purchased from Golden West Biologicals Inc. (Temecula, Calif.).

Immunoassays in 96-well microtiter plates were performed using a Tecan Genesis liquid handling robot (Center for Genomics Research, Harvard University). The following Nunc MaxiSorp polystyrene plates were used for the silver reduction and ELISA assays: clear plates for silver reduction and absorbance, black plates for fluorescence and white plates for chemiluminescence. Rabbit IgG (70 μL for each well) in ten-fold dilutions (10 μg/mL to 100 pg/mL, which corresponded to 67 nM to 670 fM) was added to the microwells, except for one row to which PBS was added as a negative control; incubation time was 2 hours. Blocking buffer (100 μL of 0.05% Tween-20 and 1% BSA in PBS) was then added, and left to incubate for 30 minutes. For secondary antibodies, dilutions (30 μL of 0.05% Tween-20 in PBS) of 1:300 anti-rabbit IgG (gold-conjugated), 1:1000 anti-rabbit IgG (alkaline phosphatase), and 1:1000 anti-rabbit IgG (horseradish peroxidase) were used; incubation time was 1 hour. For ELISA substrates, pNPP (100 μL; 3 minute incubation), AttoPhos (100 μL, used within 1 week of opening; 10 minute incubation), and SuperSignal Femto ELISA (100 μL; after 5 minutes) were used. For silver enhancement, the solutions of silver and initiator (at 4° C.) were mixed in a 1:1 ratio immediately before development; it was filtered through a 0.2 μm filter, and 100 μL was added to each well. After a 20 minute incubation, the silver enhancer solution was removed, and each well was washed with water. In general, warming the silver enhancement solution from 4° C. to room temperature increased the rate of silver deposition. In between the addition of each new reagent, each well was washed three times with PBS, with the following exception: deionized water was used to wash the wells after incubation with anti-rabbit IgG (gold) and before silver enhancement, in order to avoid precipitation of AgCl. The plate readers used were Spectramax Plus 384 for absorbance measurements, and Spectramax Gemini XS for fluorescence and chemiluminescence measurements.

The output of the optical IC was light transmittance; apparent absorbance values were calculated using the relation $A=-\log(T/T_0)$, where A is the absorbance, and T and $T_0$ are the transmission of the light through the sample and reference, respectively, to the photodetector. Air was used as the reference in the plate reader, and a blank polystyrene plate was used as the reference for the portable detector.

Figure 7:
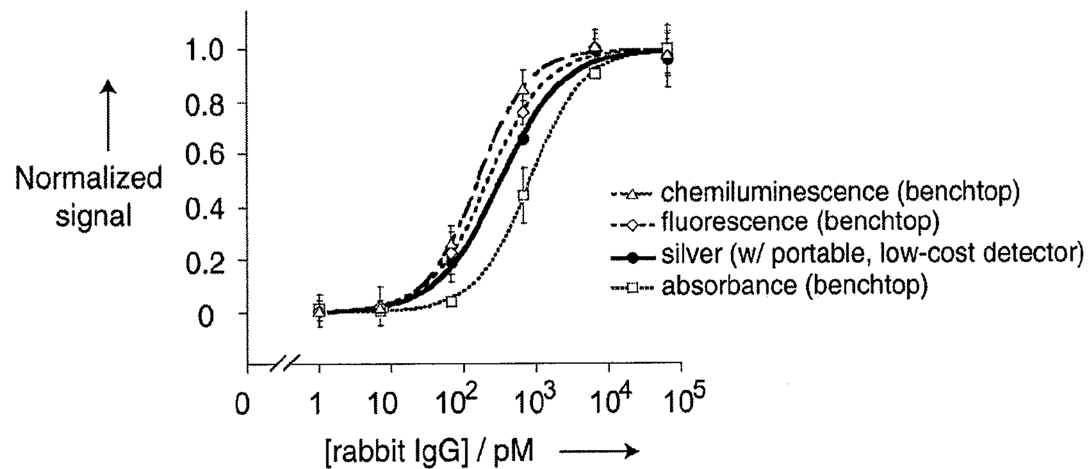
FIG. 7 provides graphical data regarding four different assay techniques.

The absorbance, fluorescence, and chemiluminescence readings (y) were fit to sigmoidal curves using the software Kaleidagraph and the following equation: $y=Ax^n/(B+x^n)+C$, where x is the concentration of the analyte, and A, B, C and n are floating parameters. Results are illustrated in FIG. 7. This equation describes a general sigmoidal curve with the lowest possible number of floating parameters (four). Curve fitting to all four titrations gave correlation coefficients of over 0.99. The readings y for all four titrations were normalized to the same scale (0 to 1) by linearly transforming each data set to achieve the values of A=1 (asymptote as x approaches infinity) and C=0 (y-intercept).

Limits of detection were calculated according to the IUPAC definition: three times the standard deviation of the blank sample ("noise") divided by the slope ("sensitivity"). In samples with no rabbit IgG (i.e., negative controls), the methods that exhibited the least to most noise were (after normalization of the signal from 0 to 1): 0.006 for absorbance of pNPP, 0.014 for chemiluminescence of SuperSignal ELISA Femto Max, 0.023 for silver (using the portable detector), and 0.066 for fluorescence of AttoPhos. The methods that showed the highest to lowest sensitivities, which were measured as slopes of the best-fit curves in the middle of the linear working range of detection (signal of 0.50), were (in normalized units per 100 pM of analyte): 0.193 for chemiluminescence, 0.121 for fluorescence, 0.078 for silver, and 0.035 for absorbance.

Figure 8:
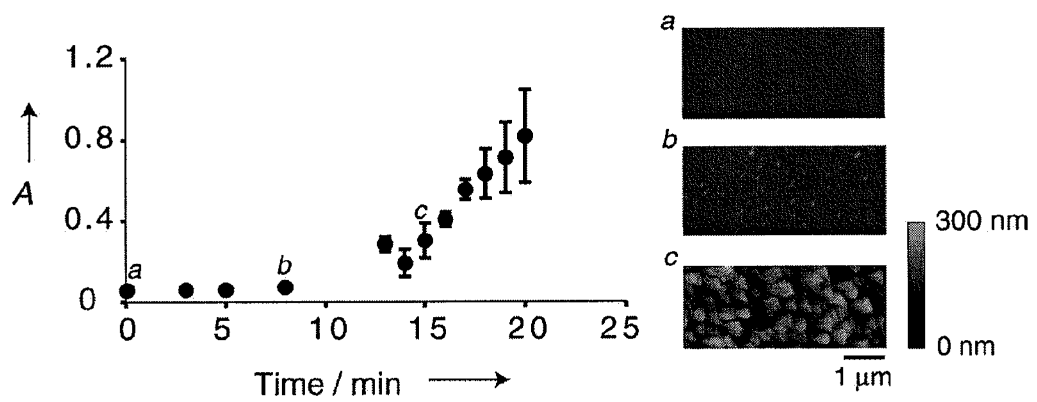
FIG. 8 provides graphical data indicating absorbance vs. time of exposure and provides photocopies of micrographs showing an opaque material.

To prepare immunoassay samples for analysis by AFM, holes (4 mm in diameter) were punched in a PDMS slab, and the PDMS slab was placed onto a polystyrene surface. Immunoassays were carried out in individual PDMS wells. After silver development, the PDMS slab was removed, and the samples on the flat polystyrene substrate were analyzed by tapping mode AFM. AFM was performed with a Dimension 3100 Scanning Probe Microscope (Digital Instruments, Santa Barbara, Calif.) in tapping mode, using silicon probes (Si #MPP-111000; NanoDevices, Santa Barbara, Calif.) at a scan rate of 0.35 Hz. AFM micrographs are provided in FIG. 8. Streaking was observed for samples with the largest silver grains, which suggested that the silver grains were loosely bound to the surface.

The microfluidic device was fabricated in PDMS using published procedures in soft lithography. The dimensions of the microchannels were 2 mm in width and 130 μm in height. The polystyrene surface was initially patterned with a stripe of HIV Env antigen (10 μg/mL) by filling a PDMS channel (conformally sealed onto the polystyrene plate) with the antigen solution. After an overnight incubation, the channel was emptied, the PDMS slab removed from the polystyrene surface, and the surface was rinsed with deionized water. The stripe of antigen was covered with an unstructured slab of PDMS, and the remaining surface of polystyrene was oxidized with oxygen plasma. After removal of the plasma-protective PDMS slab, another microfluidic channel (also freshly plasma-oxidized) was sealed orthogonally to the antigen stripe. The dimensions of these microchannels were 2 mm in width and 40 μm in height; the width of the channel must be large enough to register a signal with the portable detector. To avoid sagging of the PDMS, pillars (which took up 12% of the surface area) were included in the channel design. The anti-HIV antibody assay was carried out in the microfluidic channels with the following incubation times: 1 to 4 hours for blocking, 10 minutes for samples, 10 minutes for gold-labeled anti-human IgG, and 13.5 minutes for silver enhancement solution. After 6.5 minutes of silver enhancement, the silver solution was exchanged with a freshly prepared one. The PDMS microchannel was removed above the initial stripe of antigen before measuring the optical density of the silver film. The HIV assay in microwells were performed with the following incubation times: overnight for HIV Env antigen, 2 hours for blocking, 3 hours for samples, 1 hour for gold-labeled anti-human IgG, and 10 minutes for silver enhancement solution.

For each concentration of rabbit IgG and each dilution of human serum, triplicates of the immunoassay were performed, and average values and standard deviations were calculated.

The electronic circuit consisted of a transmitter section and a receiver section. In the transmitter section, a 1 kHz oscillator modulated the light output of a laser diode. A red semiconductor laser diode (Sharp GH06510B2A; normally used for optical data storage applications such as DVD) was used; it emitted at a wavelength of 654 nm with a maximum power of 10 mW. The laser output went through the sample to the receiver section. An optical IC (Sharp IS455; normally used in photocopy machines) was used to detect and amplify the signal. IS455 provided a linear output current with respect to the input illuminance (1 μA per lux). (The dimensions and costs of the red laser diode and the optical IC were 5.6 mm and $10, and 5.0 mm and $2, respectively.) The signal was then filtered by a second-order bandpass filter centered at 1 kHz, and its amplitude registered by a peak detector. The output of the peak detector was connected to an Analog/Digital converter that also encoded the output into binary coded decimal (Intersil ICL7106). The signal was displayed by a 3.5 digit liquid crystal display, which provided an output readout range from 0 to 1999. The entire circuitry was operated with either a 9 V battery or a single polarity 5 V source, which was inverted with a CMOS voltage converter (Intersil ICL7660) to create a ±5 V supply. To reduce the noise in the system, pulse modulation of the optical signal at 1 kHz was used to filter the noise power in the frequency spectrum; as a result, only the portion of the optical noise that fit in the pass band of the receiver filter contributed to the overall noise detected. The system could also be used without the signal modulation (i.e. at direct current)

The laser diode and optical IC were placed on two separate circuit boards that were held at a fixed orientation to ensure consistent alignment of the light path from the light source to the photodetector. Between the light source and photodetector, a glass plate was placed. A black transparency, with a pinhole aligned with the light path, was placed on the glass plate to block the transmission of stray light that did not enter the sample. To record a measurement, a polystyrene plate (either a 96-well plate or a plate with a microfluidic device) was placed onto the glass plate. The sample was aligned to the light path by roughly placing the sample over the pinhole, and finely adjusting the x and y position of the polystyrene plate until a maximum transmittance was achieved. The reading from the liquid crystal display was recorded.

To compare two detection methods independent of analyte, microwells of a 96 well plate were subjected to readings by an IC and by a commercial plate reader.

Figure 11:
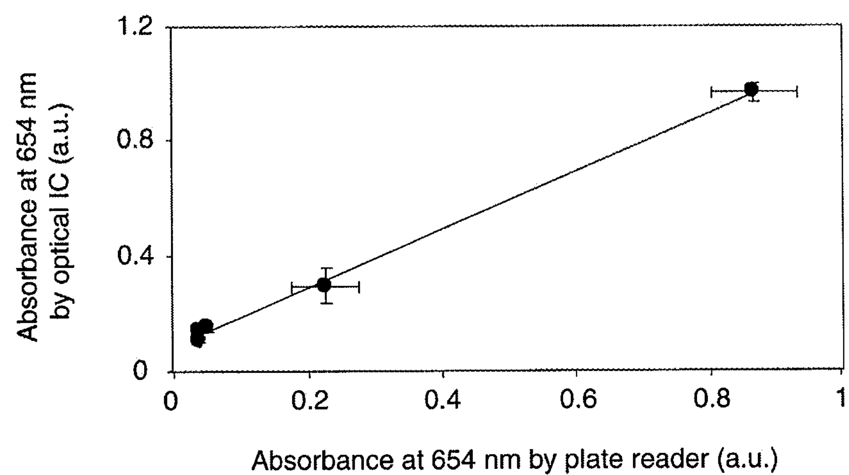
FIG. 11 provides additional graphical data comparing absorbance by two different techniques.

Absorbance of microwells containing different concentrations of BluePhos, which absorbs maximally at 600 nm, was measured by a UV-visible absorbance plate reader and the optical IC described in this study. A direct ELISA was performed on 0.67 pM to 0.67 nM of rabbit IgG as the analyte, using an anti-rabbit IgG conjugated to alkaline phosphatase and BluePhos as the phosphatase substrate. Results are provided in FIG. 10 and FIG. 11. Measurements with both devices were made at 654 nm. The best fit line by linear regression is shown (correlation coefficient of 0.998, slope of 1.01, y-intercept of 0.08). Error bars are standard deviations of measurements of three different microwells.

In this assay, in which the colorimetric product is a homogeneous solution in the microwell, the two detection methods resulted in almost perfect agreement (correlation coefficient of 0.998). Thus, inhomogeneity of silver deposition on the surface may have contributed to the imperfect agreement between the two measurement methods, such that different parts of the same well were sampled by the laser diode and by the plate reader (correlation coefficient of 0.996).

Example 2

A schematic representation of one embodiment and an optical detection device is provided in FIG. 9*a*. (A) Red light from the laser diode passes through the silver-coated microwell containing the sample to the optical IC. A pinhole was used to block stray light that did not pass through the sample. The laser diode and the optical IC were driven by the same circuit, which also had an integrated liquid crystal display that showed the measured transmittance value.

Example 3

FIG. 10 provides a comparison of readings of an immunoassay using an optical IC and a UV-visible plate reader. An immunoassay using silver reduction was performed on a 96-well plate that detected rabbit IgG. Optical micrographs of the silver films on microwells are shown for each sample. The apparent absorbance of each microwell was measured by an optical IC, and compared to its reading by a UV-visible plate reader; both measurements were made at 654 nm. The best-fit line by linear regression has a correlation coefficient of 0.989, slope of 1.12, and y-intercept of 0.16.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

What is claimed is:

1. A method comprising:

passing a fluid sample comprising a sample component over a region of a microfluidic channel, the region comprising a maximum cross-sectional dimension of less than 1 mm;

performing a chemical and/or biological reaction involving the sample component at the region of the microfluidic channel;

forming an opaque layer at the region of the microfluidic channel from a fluid flowing through the microfluidic channel;

determining the formation of the opaque layer as a function of time, wherein the determining step comprises irradiating the opaque layer with light and measuring light transmittance or light absorbance; and determining the sample component or a product of the chemical and/or biological reaction based on the formation of the opaque layer as a function of time.

2. The method of claim 1, wherein the fluid flowing through the microfluidic channel is a metal solution.

3. The method of claim 2, wherein the metal solution is a silver solution.

4. The method of claim 3, wherein the silver solution comprises silver nitrate.

5. The method of claim 1, wherein the opaque layer is a metallic layer.

6. The method of claim 1, wherein the opaque layer is a polymeric layer.

7. The method of claim 1, wherein the chemical and/or biological reaction is a binding interaction between at least two binding partners.

8. The method of claim 7, wherein the chemical and/or biological reaction is a binding interaction between the sample component and a binding partner disposed on a surface of the region.

9. The method of claim 8, wherein the binding partner is disposed across a width of the microfluidic channel.

10. The method of claim 1, comprising associating a colloid with the sample component.

11. The method of claim 10, wherein the colloid is a metal colloid.

12. The method of claim 10, wherein the colloid is a polymeric colloid.

13. The method of claim 10, comprising associating the colloid with the sample component prior to the passing step.

14. The method of claim 10, comprising associating the colloid with the sample component after the passing step.

15. The method of claim 11, wherein the metal colloid comprises gold.

16. The method of claim 11, wherein the metal colloid comprises a gold-conjugated antibody.

17. The method of claim 1, wherein the opaque layer comprises silver.

18. The method of claim 1, wherein the sample component is one of an antigen and an antibody and the binding partner is the other of the antigen and the antibody.

19. The method of claim 1, comprising determining the opacity of the opaque layer.

20. The method of claim 19, comprising quantitatively determining the opacity of the opaque layer.

21. The method of claim 1, wherein the opaque layer allows transmittance of less than 50 percent of the light irradiating the opaque layer.

22. The method of claim 1, wherein the light is measured at the same wavelength at which it is transmitted.

23. The method of claim 1, wherein the fluid sample is passed over a plurality of surfaces, and wherein the plurality of surfaces includes at least a first surface including a first binding partner disposed across the first surface and a second surface including a second binding partner disposed across the second surface, and wherein the first and second surfaces are positioned in series with respect to one another.

24. The method of claim 23, comprising flowing a metal solution over the first and second surfaces to form a first opaque layer at the first surface and a second opaque layer at the second surface.

25. The method of claim 1, wherein the fluid sample comprises whole blood.

26. The method of claim 1, wherein the region of the microfluidic channel comprises at least one cross-sectional dimension of less than 100 microns.

27. The method of claim 1, wherein the opaque layer extends across a width of the microfluidic channel.

28. The method of claim 1, wherein the opaque layer has a horizontal dimension of greater than 10 microns.

29. The method of claim 1, wherein the opaque layer has a horizontal dimension of greater than 100 microns.

30. The method of claim 1, wherein the opaque layer has a thickness of greater than 10 nanometers.

31. The method of claim 1, wherein the chemical and/or biological reaction is performed while a fluid is flowing continuously in the microfluidic channel.

32. The method of claim 1, wherein the opaque layer is continuous.

33. The method of claim 1, wherein the opaque layer is discontinuous.

34. The method of claim 1, wherein the opaque layer is a web or honeycomb of material that includes passages that allow light to be transmitted therethrough.

35. The method of claim 1, wherein each of the steps is performed while fluid is flowing in the microfluidic channel.

36. The method of claim 1, comprising applying a vacuum to an outlet of the microfluidic channel to induce fluid flow.

37. The method of claim 1, wherein the fluid flowing through the microfluidic channel is flowing continuously over the region of the microfluidic channel where the opaque layer is being formed.

38. The method of claim 1, wherein the fluid flowing through the microfluidic channel is not the fluid sample.

39. The method of claim 37, wherein the fluid flowing through the microfluidic channel is not the fluid sample.

40. The method of claim 1, wherein the region comprises a maximum cross-sectional dimension of less than 100 microns.

41. The method of claim 1, wherein the determining step comprises irradiating the opaque layer with light and measuring light transmittance.

42. The method of claim 1, further comprising flowing a rinsing solution through the microfluidic channel.

43. The method of claim 1, wherein the region of a microfluidic channel is formed of a material transparent to the light for which transmittance or absorbance is measured.

44. The method of claim 1, wherein the microfluidic channel is positioned in a microfluidic device, and wherein the microfluidic device is configured to store the fluid from which the opaque layer forms.

* * * * *

UNITED STATES PATENT AND TRADEMARK OFFICE

CERTIFICATE OF CORRECTION

PATENT NO. : 10,082,507 B2
APPLICATION NO. : 14/042606
DATED : September 25, 2018
INVENTOR(S) : Samuel K. Sia et al.

It is certified that error appears in the above-identified patent and that said Letters Patent is hereby corrected as shown below:

In the Specification

At Column 1, Lines 24-26, please change the sentence:
"This invention was sponsored by National Institute of Health grant GM30367 and National Science Foundation grant ECS-9729405. The Government has certain rights in the invention."

To:
--This invention was made with government support under GM030367 awarded by the National Institutes of Health, and 9729405 awarded by the National Science Foundation. The government has certain rights in the invention.--

Signed and Sealed this
Thirteenth Day of August, 2024

Katherine Kelly Vidal

Katherine Kelly Vidal
*Director of the United States Patent and Trademark Office*